(12) United States Patent
Sun et al.

(10) Patent No.: US 10,494,567 B2
(45) Date of Patent: Dec. 3, 2019

(54) RECOVERABLE INSTANT THICKENING ACID AND ITS REUSING METHOD

(71) Applicant: CHINA NATIONAL PETROLEUM CORPORATION CHUANQING DRILLING ENGINEERING COMPANY LIMITED CHANGQING DOWNHOLE TECHNOLOGY COMPANY, Xian, Shaanxi (CN)

(72) Inventors: Hu Sun, Shaanxi (CN); Zuwen Wang, Shaanxi (CN); Mian Zhang, Shaanxi (CN); Yan Gao, Shaanxi (CN); Xiuli Shao, Shaanxi (CN); Jing Li, Shaanxi (CN); Gaihong Wang, Shaanxi (CN); Dongrui Yuan, Shaanxi (CN); Zhiming Jing, Shaanxi (CN); Junfang Xu, Shaanxi (CN)

(73) Assignee: CHINA NATIONAL PETROLEUM CORPORATION CHUANQING DRILLING ENGINEERING COMPANY LIMITED CHANGQING DOWNHOLE TECHNOLOGY COMPANY, Xian (CN)

( * ) Notice: Subject to any disclaimer, the term of this patent is extended or adjusted under 35 U.S.C. 154(b) by 89 days.

(21) Appl. No.: 15/572,036

(22) PCT Filed: May 8, 2015

(86) PCT No.: PCT/CN2015/078533
§ 371 (c)(1),
(2) Date: Nov. 6, 2017

(87) PCT Pub. No.: WO2016/179742
PCT Pub. Date: Nov. 17, 2016

(65) Prior Publication Data
US 2018/0142138 A1 May 24, 2018

(51) Int. Cl.
C09K 8/74 (2006.01)
E21B 49/08 (2006.01)
C07C 69/02 (2006.01)

(52) U.S. Cl.
CPC ............... *C09K 8/74* (2013.01); *E21B 49/08* (2013.01); *C07C 69/02* (2013.01); *E21B 2049/085* (2013.01)

(58) Field of Classification Search
None
See application file for complete search history.

(56) References Cited

U.S. PATENT DOCUMENTS 4,215,001 A * 7/1980 Elphingstone ......... C09K 8/665
166/307
6,291,406 B1 * 9/2001 Rose ....................... C09K 8/28
507/239

(Continued)

FOREIGN PATENT DOCUMENTS

CN 101994504 3/2011
CN 102851018 1/2013

(Continued)

OTHER PUBLICATIONS

International search report dated Feb. 4, 2016 from corresponding application No. PCT/CN2015/078533.

*Primary Examiner* — John J Figueroa
(74) *Attorney, Agent, or Firm* — Hauptman Ham, LLP

(57) ABSTRACT

A recoverable instant thickening acid and its reusing method is usable for the recycling and reusing of a gas well carbonate reservoir acidizing fluid and production stimulation operation. The recoverable instant thickening acid includes the following components in weight percentage: 1.5-3 parts of a thickener, 0.5-3 parts of potassium chloride and 100 parts of a hydrochloric acid solution, wherein the thickener is a mixture composed of a mass ratio of 40%-70%

(Continued)

of N-lauryl-N'-hydroxyethyl-N'-hydroxypropyl ethylenediamine propionate or its derivatives, 4%-12% of ethanol and 18%-56% of water. With the thickening acid for performing an acidizing treatment, the residual acid solution can be re-prepared as a thickening acid for an acidizing treatment without a chemical treatment, assisting the green and environmentally friendly production and sustainable development of gas fields.

6 Claims, 2 Drawing Sheets

(56) References Cited

U.S. PATENT DOCUMENTS

2005/0126786 A1\* 6/2005 Fu ............................ C09K 8/74
166/307
2012/0302470 A1\* 11/2012 Pollard .................... C09K 8/52
507/261

FOREIGN PATENT DOCUMENTS

| CN | 103305208 | 9/2013 |
| CN | 104861957 | 8/2015 |

\* cited by examiner

RECOVERABLE INSTANT THICKENING ACID AND ITS REUSING METHOD

RELATED APPLICATIONS

The present application is a National Phase of International Application Number PCT/CN2015/078533, filed May 8, 2015.

FIELD OF THE INVENTION

The present invention relates to a recoverable instant thickening acid, which is mainly used for recovering and reusing the acidification solution of the carbonate reservoir for the gas well.

BACKGROUND

A thickening acid is the main acid system of the acidification of the Lower Paleozoic carbonate reservoirs in CHANGQING gas field, which has high viscosity and good retarded, seam-making performance, long acid etching effect and good modification effect. However, the current thickening acid used in CHANGQING gas field exits problems that acidified residual acid solution can not be recycled, and a thickening time is long and other issues.

Since Schlumberger Dowell had introduced a viscoelastic surfactant-based cleaning fracturing fluid in 1997, the advent of viscoelastic surfactant technology has been widely used and promoted in the oil and gas field production measures. Domestic reports of cleaning fracturing fluids are not uncommon, and cleaning fracturing fluids are popular in oilfield applications because they are easy to prepare, without the need for adhesives and breakers, no damage and good for maintaining the permeability of the proppant pack compared to conventional polymer fracturing fluids. According to the experience of VES, a amphoteric surfactant-based viscoelastic acid which has a superior performance has developed in abroad in the past two years, and is successfully used in acid-fracturing. But the acid can not be recycled.

In the face of the increase in the proportion of compact carbonate reservoir resources, it is urgent to find new technologies to enhance the modification effect of compact carbonate reservoirs. In 2014, CHANGQING Oilfield Company developed a new type of cleaning thickening acid system, the system has good heat resistance, shear resistance, low filtration loss, slow speed, good corrosion inhibition performance, capable of continuous mixing and cleaning low damage and other performances and advantages. However, the thickening acid has a long thickening time and can not be recycled.

At present, research and application of the recovery of surfactant thickening acid has not yet appeared in the domestic, therefore there is of great prospect to develop and apply the direct mixing of the surfactant thickening acid and the reuse of residual acid.

SUMMARY

In order to solve the above-mentioned technical problems, the present invention provides a recoverable instant thickening acid. An acidizing treatment with preparing and pouring at the same time can be realized by using the recoverable instant thickening acid. After the acidizing treatment, the gel breaking and flowback acid can be reused to prepare the thickening acid without chemical treatment, so as to ensure a green production and a sustainable development of the gas field.

The present invention is achieved by adopting the following technical scheme:

A recoverable instant thickening acid which is prepared from the following components in the following proportions of the quality components:

Thickener: 1.5 to 3 parts;
Potassium chloride: 0.5 parts to 3 parts;
Hydrochloric acid solution: 100 parts.

The thickening agent is a mixture by mixing a mass ratio of 40% to 70% N-lauryl-N'-hydroxyethyl-N'-hydroxypropyl ethylenediamine propionate or its derivatives, 4 to 12% ethanol and 18 to 56% water.

The hydrochloric acid solution has a mass concentration of 15 to 30%.

The recoverable instant thickening acid has a thickening time of less than 30 s and a viscosity of at least 60 mPa·s at normal temperature on the ground; the viscosity ≤15 mPa·s with a stratum temperature greater than 105° C.; the viscosity ≤5 mPa·s with the stratum temperature greater than 120° C.

Advantageous effects of the present invention:

1. The recoverable instant thickening acid of the present invention has a high speed of thickening and can be used for acidizing treatment with preparing and pouring at the same time.

2. The recoverable instant thickening acid of the present invention has a viscosity of at least 60 mPa·s at normal temperature on the ground (25° C.), reducing the filtration loss of the thickening acid.

3. The recoverable instant thickening acid of the present invention has a viscosity of at least 60 mPa·s at normal temperature on the ground (25° C.), a viscosity of ≤15 mPa·s when the stratum temperature is greater than 105° C., and the viscosity ≤5 mPa·s at 120° C., which is conducive to the flowback of residual acid.

4. According to the recoverable instant thickening acid of the present invention, the acidified flowback fluid enter into a acid tank via gas-liquid separation, and residual acid solution and thickener are separated as two layers after 2 hours and are collected respectively, and then add a small amount of thickener, hydrochloric acid and potassium chloride to form a recoverable instant thickening acid; which reduce the thickener, hydrochloric acid, water, while reducing the cost of treatment work, theoretically the technology can be achieved 3 times for acidification works.

5. The recoverable instant thickening acid of the present invention ensures that its viscosity of is at least 60 mPa·s at ambient temperature on the ground (25° C.), and is ≤15 mPa·s when the stratum temperature is greater than 105° C., is ≤5 mPa·s when the stratum temperature is 120° C., which is conducive to the viscosity adjustment of the recoverable instant thickening acid.

The invention will now be described in further detail with reference to the accompanying drawings.

DESCRIPTION OF THE EMBODIMENTS

Example 1

Figure 1:
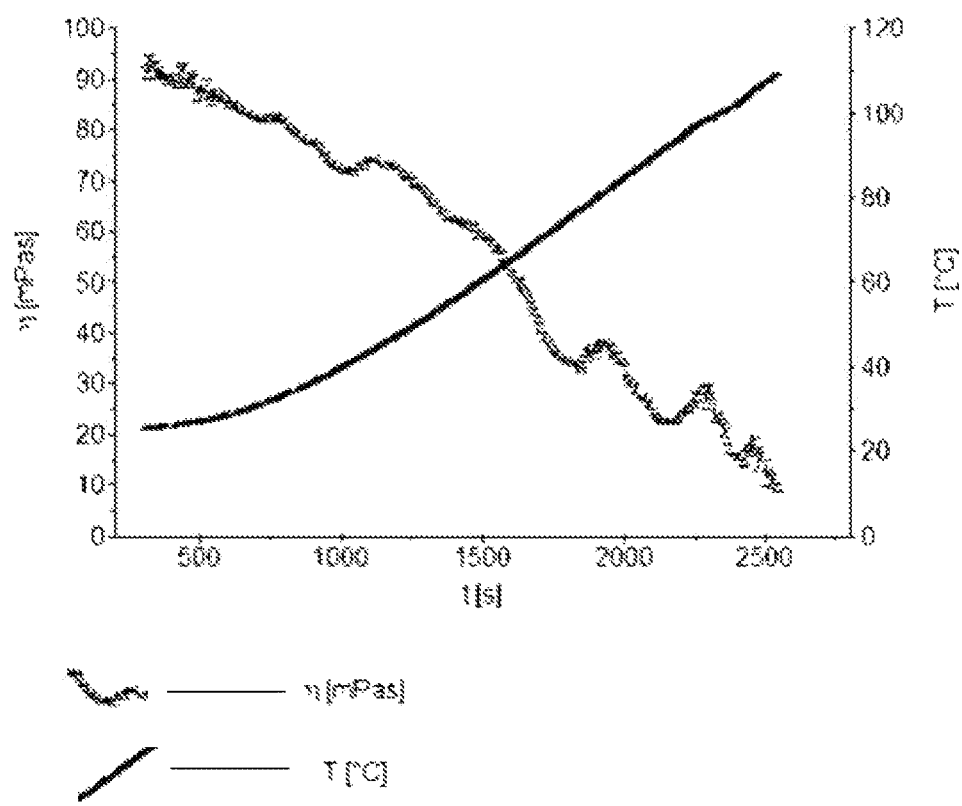
FIG. 1 is a graph showing the change in the temperature resistance T and the viscosity value η of the original acid solution over time.

The present embodiment provides a recoverable instant thickening acid which is prepared from the following components in the following proportions of the quality components:

Thickener: 1.5 parts;
Potassium chloride: 0.5 part;
Hydrochloric acid solution: 100 parts.

The above thickener is a mixture consisting of a mass ratio of 55% N-lauryl-N'-hydroxyethyl-N'-hydroxypropyl ethylenediamine propionate or its derivatives, 8% ethanol and 37% water.

The above hydrochloric acid solution has a mass concentration of 15%.

The thickening time of this recoverable instant thickening acid is less than 30 s, the viscosity is at least 60 mPa·s at normal temperature on the ground. When the stratum temperature is above 105° C., the viscosity ≤15 mPa·s; at 120° C., the viscosity ≤5 mPa S.

One recoverable instant thickening acid prepared by this example has been measured and tested. And its thickening time is 15 s at normal temperature on the ground (25° C.), its viscosity is 83 mPa·s, and its temperature resistance is up to 102° C., which are in accordance with the repeated acidizing operating conditions of the present invention.

Example 2

The present embodiment provides a recoverable instant thickening acid which is prepared from the following components in the following proportions of the quality components:

Thickener: 2 parts;
Potassium chloride: 1 part;
Hydrochloric acid solution: 100 parts.

The above thickener is a mixture consisting of a mass ratio of 48% N-lauryl-N'-hydroxyethyl-N'-hydroxypropyl ethylenediamine propionate or its derivatives, 10% ethanol and 42% water.

The above hydrochloric acid solution has a mass concentration of 20%.

The thickening time of this recoverable instant thickening acid is less than 30 s, the viscosity is at least 60 mPa·s at normal temperature on the ground. When the stratum temperature is above 105° C., the viscosity ≤15 mPa·s; at 120° C., the viscosity ≤5 mPa S.

One recoverable instant thickening acid prepared by this example has been measured and tested. And its thickening time is 12 s at normal temperature on the ground (25° C.), its viscosity is 94 mPa·s, and its temperature resistance is up to 106° C., which are in accordance with the repeated acidizing operating conditions of the present invention and are more effective than those of Example 1.

Example 3

The present embodiment provides a recoverable instant thickening acid which is is prepared from the following components in the following proportions of the quality components:

Thickener: 2.5 parts;
Potassium chloride: 2 parts;
Hydrochloric acid solution: 100 parts.

The above thickener is a mixture consisting of a mass ratio of 63% N-lauryl-N'-hydroxyethyl-N'-hydroxypropyl ethylenediamine propionate or its derivatives, 6% ethanol and 31% water.

The above hydrochloric acid solution has a mass concentration of 25%.

One recoverable instant thickening acid prepared by this example has been measured and tested. And its thickening time is 18 s at normal temperature on the ground (25° C.), its viscosity is 80 mPa·s, and its temperature resistance is up to 107° C., which are in accordance with the repeated acidizing operating conditions of the present invention. Compared with the example 1 and example 2, the temperature resistance is improved, however viscosity and thickening time are less effective than those of the former two.

Example 4

The present embodiment provides a recoverable instant thickening acid which is prepared from the following components in the following proportions of the quality components:

Thickener: 3 parts;
Potassium chloride: 3 parts;
Hydrochloric acid solution: 100 parts.

The above thickener is a mixture consisting of a mass ratio of 51% N-lauryl-N'-hydroxyethyl-N'-hydroxypropyl ethylenediamine propionate or its derivatives, 9% ethanol and 40% water.

The above hydrochloric acid solution has a mass concentration of 30%.

One recoverable instant thickening acid prepared by this example has been measured and tested. And its thickening time is 20 s at normal temperature on the ground (25° C.), its viscosity is 63 mPa·s, and its temperature resistance is up to 103° C., which are in accordance with the repeated acidizing operating conditions of the present invention and are less effective than those of the former three examples.

Example 5

The different proportions of the four embodiments described above obtain acids which has some different in the performances, and the acids may be carried out in the following steps:

a. Directly mixed the thickener, potassium chloride and hydrochloric acid solution together into the blender to form a recoverable instant thickening acid;

b. Press the recoverable instantly thickening acid at step a into the gas well stratum at a temperature of 0° C. to 110° C., to carry out acidizing treatment;

c. Shut down the gas well for 30 min after the end of acidification, then control blowout;

d. Discharge the blowout residual acid solution into a acid tank, and after standing for 2 hours and layering, the residual acid solution and the thickener are collected into different acid tanks respectively;

e. Determine the viscosity of the thickener and the concentration of hydrochloric acid in the residual acid solution. If the viscosity of the thickener does not meet the design requirements of the original thickener, the thickener is added until the viscosity meets the requirements. If the concentration of hydrochloric acid in the residual acid solution does not meet the concentration requirements of the original hydrochloric acid solution, continue to add a high concentration of hydrochloric acid (the high concentration of hydrochloric acid has a concentration of 36~38%) until the acid concentration meet the requirements;

f. The thickener and the hydrochloric acid solution obtained in step e are mixed with potassium chloride and pumped into the blender, and then injected into the stratum for acidizing treatment once again;

g. Repeat steps a through f to complete the reuse of acid.

Example 6

The present embodiment was carried out in the same manner as in Example 5, and the is acids of the different proportions of the components prepared in Examples 1 to 4 was carried out by the method proposed in Example 5 to obtain the corresponding effect data:

First, the lateral alignment analysis was carried out. Using the results of the preparation of the components of the recoverable instant thickening acid in the above four examples, the analysis results are shown as follows:

| type | thickener/% | KCl/% | HCl/% | viscosity/ mPa·s | temperature resistance/□ | thickening time/s |
|---|---|---|---|---|---|---|
| Example 1 | 1.5 | 0.5 | 15 | 83 | 102 | 15 |
| Example 2 | 2.0 | 1.0 | 20 | 94 | 106 | 12 |
| Example 3 | 2.5 | 2.0 | 25 | 80 | 107 | 18 |
| Example 4 | 3.0 | 3.0 | 30 | 63 | 103 | 20 |

As can be seen from the data in the above table, the ratio in Example 2 is the optimum ratio, and the experimental results of Example 2 have a relatively large viscosity value, a shorter thickening time and a relatively strong temperature resistance than those of the other three embodiments, so the use of this ratio of the recoverable instant thickening acid for acidification, can achieve better acidification effect, a higher rate and better effect of the reuse.

Figure 2:
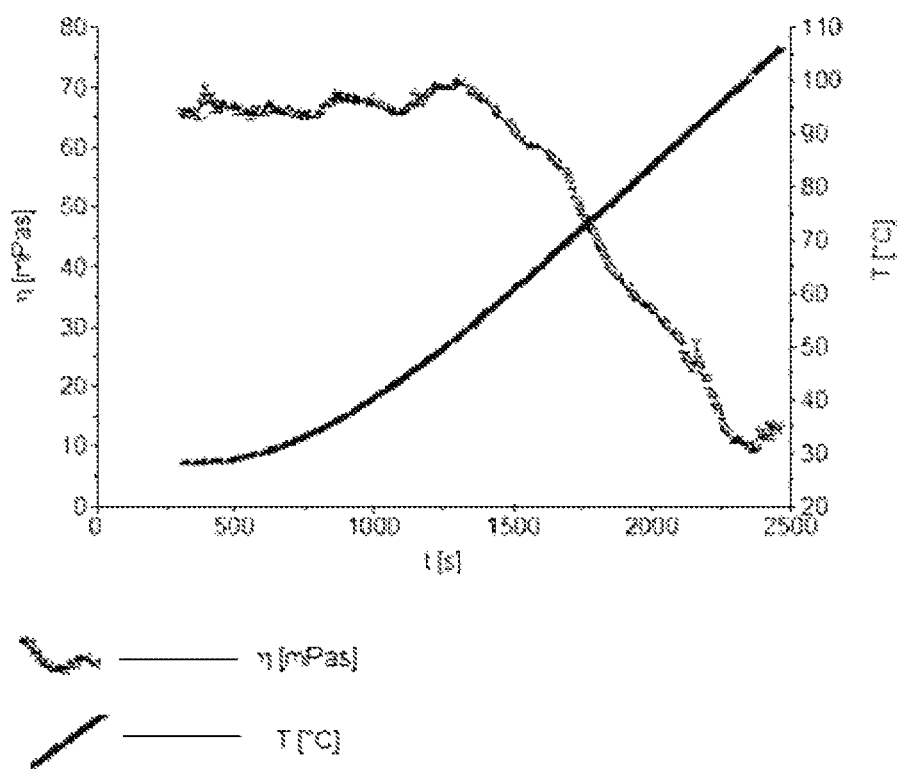
FIG. 2 is a graph showing the change in the temperature resistance T and the viscosity value η of residual acid solution with time.

In the present embodiment, longitudinal ratio analysis can also be carried out using comparisons of the temperature resistance curve and the viscosity value of the original acid solution (i.e., the recoverable instant thickening acid in step a) and the residual acid solution (i.e., the residual acid solution obtained in step e), as shown in FIG. 1 and FIG. 2. FIG. 1 is a graph showing the change in the temperature resistance T and the viscosity value η of the original acid solution over time, while FIG. 2 is a graph showing the change in the temperature resistance T and the viscosity value η of residual acid solution with time. Compared with FIG. 1 and FIG. 2, it may be shown that the temperature resistance and is the viscosity value of the residual acid solution compared with those of the original acid have little declined, but the difference is not very small. It is possible to obtain a similar effect by adding a certain amount of a high-concentration original component at the decreasing of the temperature resistance and the viscosity value. Therefore, the residual acid solution of the present invention can also be used in an acidification work. Thus, the recoverable instant thickening acid of the present invention can be repeatedly used in the acidification work. And no residual liquid is discharged to the ground, which reduces the surface pollution. And the flowback fluid can be reused and the treatment work cost is reduced. The present invention can realize the "zero discharge" of the flowback fluid after acidification, and the reuse can reduce the comprehensive cost of the thickening acid, and the large-scale popularization and application can greatly reduce the environmental pollution of the thickening acid.

The foregoing is merely illustrative of the present invention and is not to be construed as limiting the scope of the invention, and the same or similar design to the invention is within the scope of the invention.

What is claimed is:

1. A recoverable instant thickening acid, consisting of the following components in the following proportions of the quality components: 1.5 to 3 parts of thickener; 0.5 to 3 parts of potassium chloride; 100 parts of hydrochloric acid solution, wherein the thickener is a mixture by mixing a mass ratio of 40% to 70% N-lauryl-N'-hydroxyethyl-N'-hydroxypropyl ethylenediamine propionate or its derivatives, 4 to 12% ethanol and 18 to 56% water.

2. The recoverable instant thickening acid according to claim 1, wherein the hydrochloric acid solution has a mass concentration of 15 to 30%.

3. The recoverable instant thickening acid according to claim 1, wherein the recoverable instant thickening acid has a thickening time of less than 30 s and a viscosity of at least 60 mPa·s at normal temperature on the ground; the viscosity ≤15 mPa·s with a stratum temperature greater than 105° C.; the viscosity ≤5 mPa·s with the stratum temperature greater than 120° C.

4. The recoverable instant thickening acid according to claim 2, wherein the recoverable instant thickening acid has a thickening time of less than 30 s, a viscosity of at least 60 mPa·s at normal temperature on the ground, the viscosity ≤15 mPa·s with a stratum temperature greater than 105° C. and the viscosity ≤5 mPa·s with the stratum temperature greater than 120° C.

5. A method of reusing a recoverable instant thickening acid which consists of the following components in the following proportions of the quality components: 1.5 to 3 parts of thickener; 0.5 to 3 parts of potassium chloride; 100 parts of hydrochloric acid solution, including following steps:
   a. Directly mix the thickener, potassium chloride and hydrochloric acid solution together to form a recoverable instant thickening acid;
   b. Press the recoverable instantly thickening acid at the step a into the gas well stratum at a temperature of 0° C. to 110° C., to carry out acidizing treatment;
   c. Shut down the gas well after the end of acidification, then control blowout;
   d. Discharge the blowout residual acid solution into a acid tank, and after standing and layering, the residual acid solution and the thickener are collected into different acid tanks respectively;
   e. Determine the viscosity of the thickener and the concentration of hydrochloric acid in the residual acid solution, if the viscosity of the thickener does not meet the design requirements of the original thickener, the thickener is added until the viscosity meets the requirements; if the concentration of hydrochloric acid in the residual acid solution does not meet the concentration requirements of the original hydrochloric acid solution, continue to add a high concentration of hydrochloric acid until the acid concentration meet the requirements;
   f. The thickener and the hydrochloric acid solution obtained in step e are mixed with potassium chloride a, and then injected into the stratum for acidizing treatment once again;
   g. Repeat steps a through f to complete the reuse of acid.

6. The method according to claim 5, wherein the high concentration of hydrochloric acid has a concentration of 36~38%.

* * * * *